US010765335B2

(12) United States Patent
Shibata

(10) Patent No.: US 10,765,335 B2
(45) Date of Patent: Sep. 8, 2020

(54) BIOMEDICAL ELECTRODE

(71) Applicant: PROKIDAI CO., LTD., Soraku-gun, Kyoto (JP)

(72) Inventor: Kazuaki Shibata, Soraku-gun (JP)

(73) Assignee: PROKIDAI CO., LTD., Kyoto (JP)

( * ) Notice: Subject to any disclaimer, the term of this patent is extended or adjusted under 35 U.S.C. 154(b) by 446 days.

(21) Appl. No.: 15/531,599

(22) PCT Filed: Nov. 25, 2015

(86) PCT No.: PCT/JP2015/083064
§ 371 (c)(1),
(2) Date: May 30, 2017

(87) PCT Pub. No.: WO2016/093061
PCT Pub. Date: Jun. 16, 2016

(65) Prior Publication Data
US 2017/0333696 A1 Nov. 23, 2017

(30) Foreign Application Priority Data

Dec. 8, 2014 (JP) .................................. 2014-247971

(51) Int. Cl.
*A61B 5/0408* (2006.01)
*A61N 1/04* (2006.01)
*A61B 5/00* (2006.01)

(52) U.S. Cl.
CPC ...... *A61B 5/04085* (2013.01); *A61B 5/04087* (2013.01); *A61B 5/68335* (2017.08);
(Continued)

(58) Field of Classification Search
CPC .............. A61B 5/0408; A61B 5/04086; A61B 5/04087
(Continued)

(56) References Cited

U.S. PATENT DOCUMENTS 4,838,273 A 6/1989 Cartmell
4,865,582 A 9/1989 Sibalis
(Continued)

FOREIGN PATENT DOCUMENTS

EP  0293893 A2  12/1988
JP  5-070552 A  3/1993
(Continued)

OTHER PUBLICATIONS

Extended European Search Report dated Jun. 7, 2018, issued in European Patent Application No. 15866948.1.
(Continued)

*Primary Examiner* — Lee S Cohen
(74) *Attorney, Agent, or Firm* — Westermann, Hattori, Daniels & Adrian, LLP

(57) ABSTRACT

To provide a biomedical electrode which is capable of restraining displacement or release of the electrode even if a living body takes a hard action, and which is mountable without an occurrence of discomfort. This biomedical electrode has conductive gels 11, 11, retaining members 12, 12 to retain the conductive gels 11, 11, and an adhesive surface 31a, and comprises a sheet-shaped adhesive member 30 to adhere the conductive gels 11, 11 to a living body surface S via the retaining members 12, 12, and further, the adhesive member 30 is formed in an enough size to cover substantially all regions of the retaining members 12, 12, and is configured to have liquid through holes 30b to 30b, 30c, 30c to discharge sweat which is accumulated in internal spaces R, R formed between the living body surface S and the retaining members 12, 12.

7 Claims, 13 Drawing Sheets

(52) U.S. Cl.
CPC ............. *A61N 1/04* (2013.01); *A61N 1/0476* (2013.01); *A61N 1/0496* (2013.01); *A61B 2562/125* (2013.01); *A61N 1/0424* (2013.01)

(58) Field of Classification Search
USPC .................................................. 600/391, 392
See application file for complete search history.

(56) References Cited

U.S. PATENT DOCUMENTS

| | | | |
|---|---|---|---|
| 4,947,853 A | 8/1990 | Hon | |
| 8,862,199 B2 * | 10/2014 | Ko | A61B 5/04 600/372 |
| 9,861,289 B2 * | 1/2018 | Li | A61B 5/6833 |
| 2013/0325096 A1 | 12/2013 | Dupelle et al. | |
| 2014/0100432 A1 | 4/2014 | Golda et al. | |
| 2015/0119728 A1 * | 4/2015 | Blackadar | A61B 5/7264 600/484 |

FOREIGN PATENT DOCUMENTS

| | | |
|---|---|---|
| JP | 6-245913 A | 9/1994 |
| JP | 2000-126145 A | 5/2000 |
| JP | 2008-212487 A | 9/2008 |
| JP | 2012-183302 A | 9/2012 |
| JP | 2014-8166 | 1/2014 |
| WO | 2014/055994 A1 | 4/2014 |

OTHER PUBLICATIONS

International Search Report dated Feb. 23, 2016, issued in counterpart International Application No. PCT/JP2015/083064 (2 pages).
European Search Report dated Dec. 12, 2019, issued in counterpart European patent application No. 15 866 948.1. (6 pages).

* cited by examiner

BIOMEDICAL ELECTRODE

TECHNICAL FIELD

The present invention relates to a biomedical electrode which is mounted to a living body surface.

BACKGROUND ART

Conventionally, there is employed a biomedical electrode which is attached to a living body surface in order to detect a weak current generated in a living body to convey the detected current to a measuring instrument such as a heart rate monitor or convey an electric stimulus from a stimulation device such as a low frequency therapeutic device to the living body. For example, in Patent Literature 1, there is disclosed a biomedical electrode which is composed of: a conductive member having adhesiveness; an electronically conductive layer; and a nonconductive sheet-shaped material to support the layer and a connection terminal for connecting to an external device, in which a plurality of electrodes electrically independent of each other have been integrated with each other via the sheet-shaped material. Such a biomedical electrode is mounted to the living body surface by an adhesive force of the conductive member, and in general, is electrically connected to the external device such as the measuring instrument or the stimulation device via a cable which has been connected to the connection terminal.

In addition, there, is also employed an electrode which is integrated with a belt and then is mounted to a living body by winding and securing the belt to a chest part of a living body, in a case where the electrode is mounted to the chest part and then is employed with the heart rate monitor being connected thereto, etc. (For example, refer to Patent Literature 2.)

CITATION LIST

Patent Literature

Patent Literature 1: JP-U H05-070552
Patent Literature 2: JP-A H06-245913

SUMMARY OF THE INVENTION

Problems to be Solved by the Invention

However, in a case where the biomedical electrode is mounted to the living body surface by the adhesive force of the conductive member, there may be a case in which be that the electrode is released due to an action of the living body, only at the adhesive force of the conductive member. In particular, it is difficult to normally maintain functions of the electrode in a case where the electrode is continuously adhered for a long period of time, or alternatively, in a case where the electrode is used when a hard action is taken at the time of sports or the like. Further, at the time of sports or the like, it is cumbersome to connect the connection terminal of the electrode and the external device to each other via the cable; and therefore, there may also be a case in which an external device of a small size is mounted to the connection terminal; and however, in a case where the external device is thus directly attached to the living body surface, there is a need to support the external device by the biomedical electrode as well.

Accordingly, in the case where the biomedical electrode is continuously mounted to the living body surface for a long period of time or in the case where the electrode is used when a hard action is taken, it is considered that the electrode is mounted to the living body surface by employing a tape having an adhesive surface; and however, if the electrode is mounted by the tape, sweat is accumulated in an internal space between the living body surface and a member for retaining the conductive member that is covered with the tape, and there may be a case in which a release of the tape arises due to lowering of the adhesive force of the tape exerted by moisture of the sweat or due to inflation of the conductive member, or alternatively, in a case where a plurality of conductive members are provided, there is an apprehension of electric conduction between the conductive members due to the accumulated sweat as well, and consequently, the functions of the electrode cannot be maintained.

On the other hand, in the case where the biomedical electrode is secured to the body by the belt as well, there may be a case in which it becomes difficult to appropriately mount the electrode at a predetermined position depending on the shape of the living body surface, there is a problem that displacement of the electrode exerted by shifting of the belt or discomfort exerted by tightening of the belt may arise, or alternatively, there is an apprehension that the belt and a portion of linking the belt may be released from each other due to a hard action.

The present invention has been made in view of the problems described above, and it is an object of the present invention to provide a biomedical electrode which is capable of restraining displacement or release of the electrode even if a living body takes a hard action, and which is free from discomfort in a case where the electrode is mounted for a long period of time or in a case where the electrode is mounted at the time of exercise as well.

Means For Solving the Problem

In order to achieve the object described above, the present invention employs the following means.

That is, a biomedical electrode of the present invention comprises: a conductive member; a retaining member to retain the conductive member; and a sheet-shaped adhesive member having an adhesive surface, adhering the conductive member to a luring body surface via the retaining member, and is characterized in that the adhesive member is formed in an enough size to cover substantially all regions of the retaining member, and has a liquid through hole to discharge sweat which is accumulated in an internal space formed between the living body surface and the retaining member.

Here, in the present application, the wording "internal space between the living body surface and the retaining member" includes a small space between the adhesive member and the living body surface which is produced due to thickness of the retaining member, coming contact with an outer edge of the retaining member.

According to such a construction, when the conductive member is adhered to the living body surface via the retaining member, the surface is adhered by the adhesive member that covers substantially all regions of the retaining member; and therefore, even if the living body takes a hard action, it is possible to restrain displacement or release of the conductive member. In addition, the electrode is merely secured by the adhesive member; and therefore, such discomfort as felt in the case where the electrode is mounted by the belt does not arise, and in the case where the electrode is mounted at the time of sports, it is possible to concentrate on the athletic sports. Further, the electrode has the liquid through hole to discharge the sweat that is accumulated in the internal space between the living body surface and the retaining member, and the sweat that is accumulated in the internal space is pushed out from the liquid through hole due to the action of the living body, thus making it possible to restrain release of the adhesive member from an adjacent portion to the internal space due to the sweat that is accumulated in the internal space. In addition, in the case where the plurality of conductive members are provided, it is possible to prevent electric conduction between the conductive members due to the moisture of the sweat.

In addition, in order to enable mounting or demounting of the external device in a state in which the conductive member has been mounted to the living body surface and to enable reuse of the retaining member by replacing only the adhesive member with its replacement when the biomedical electrode is repeatedly mounted to, or demounted from, the living body surface, it is preferable that the retaining member retain the conductive member at a living body surface side and the connection terminal to electrically connect to the conductive member be provided at an opposite living body surface side, and the adhesive member have a through hole to protrude the connection terminal and be releasable from the retaining member.

Further, in order to easily perform positioning when adhering the retaining member to the adhesive member, it is effective that the adhesive member is able to release a sheet-shaped protection member which protects the adhesive surface so that the adhesive surface is thereby exposed, and the protection member is divided into the shape along the retaining member.

Furthermore, in order to more easily perform positioning when adhering the retaining member to the adhesive member while restraining the release of the adhesive member due to sweat, it is effective that a through hole is provided in the retaining member, and the liquid through hole having been provided in the adhesive member overlaps the through hole having been provided in the retaining member to thereby communicate with the internal space.

In order to stably retain the conductive member and restrain an increase of the internal space between the retaining member and the living body surface due to the thickness of the conductive member and easy accumulation of the sweat in the internal space, it is desirable that the retaining member form a dual structure in which a first retaining member and a second retaining member at the opposite living body surface side are bonded with each other, a cylindrical retaining space be formed of: a hole which is provided in the first remaining member; and a surface of the second retaining member at the living body surface side, and the conductive member be retained in the retaining space.

In addition, in order to more effectively restrain accumulation of the sweat in the internal space and easily perform positioning when the first retaining member and the second retaining member are bonded with each other, it is preferable that the retaining member comprises at least three through hole.

Further, in a case where the external device such as the heart rate monitor is directly mounted to the living body surface, in order to improve traceability of the conductive member with respect to the living body and restrain the release of the conductive member from the living body, it is effective that two conductive members are provided, the two conductive members are respectively arranged to be more outward than the corresponding connection terminals, and the conductive members and the corresponding connection terminals are electrically connected to each other by means of conductive ink that has been printed on the retaining member.

Furthermore, in order to improve traceability of the conductive members with respect to the living body, it is also effective that the retaining member is separated as to each of the conductive members.

Effect of the Invention

According to the present invention described hereinabove, it is possible to provide a biomedical electrode which is capable of restraining displacement or release of the electrode, even if a living body takes a hard action, and which is free from discomfort in a case where the electrode is mounted for a long period of time or in a case where the electrode is mounted at the time of exercise as well.

MODE FOR CARRYING OUT THE INVENTION

Hereinafter, biomedical electrodes according to embodiments of the present invention will be described with reference to the drawings.

First Embodiment

Figure 1:
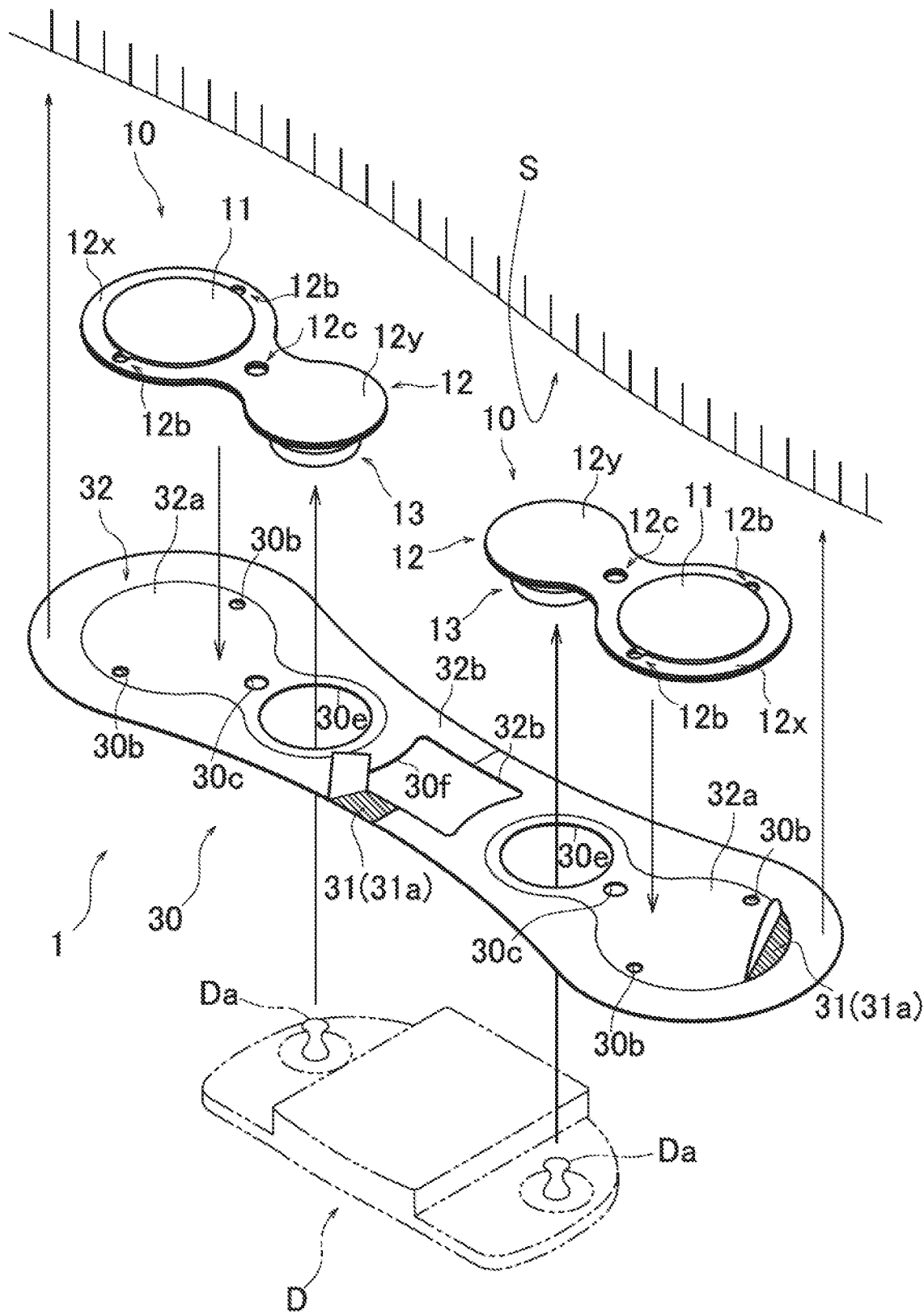
FIG. 1 is an exploded perspective view of a biomedical electrode according to a first embodiment of the present invention.

FIG. 1 is a perspective view of a biomedical electrode 1 according to a first embodiment of the present invention. As shown in the figure, the biomedical electrode 1 is mainly composed of two electrode main bodies 10, 10 and an adhesive member 30; is mounted by being adhered to a living body surface S in a state in which the electrode main bodies 10, 10 have been adhered to the adhesive member 30; and is employed, in this state, by directly attaching an external device D such as a heart rate monitor to the living body surface S.

In a case where a description of directions is furnished hereinafter, the living body surface S side with respect to the biomedical electrode 1 is defined as a living body surface direction; an opposite side thereto is defined as an opposite living body surface direction; in a plane which is substantially parallel to the living body surface S, a direction in which the two electrode main bodies 10 are arranged is defined as a longitudinal direction; and a perpendicular direction thereto is defined as a transverse direction.

In addition, the two electrode main bodies 10, 10 have the same construction, and hereinafter, one electrode main body 10 will be described.

Figure 2:
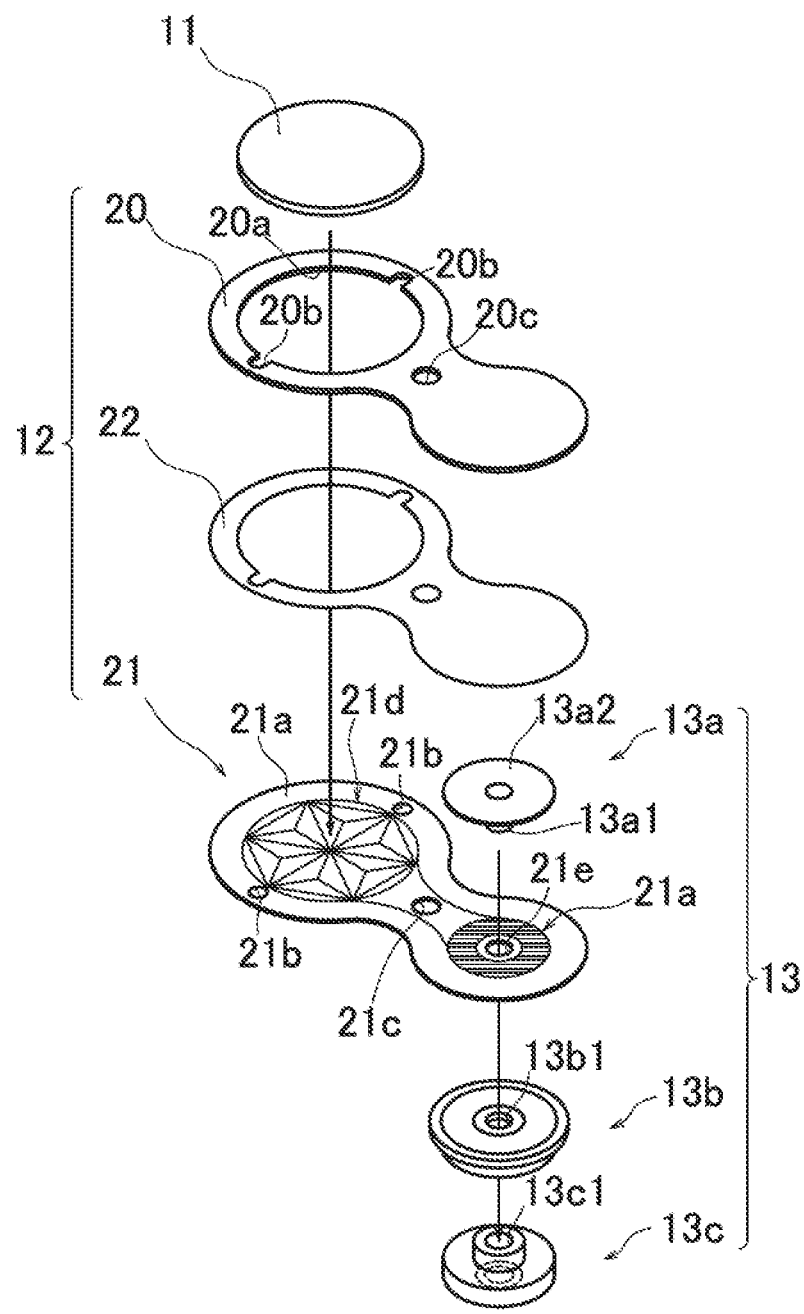
FIG. 2 is an exploded perspective view of an electrode main body of the biomedical electrode.
Figure 3A:
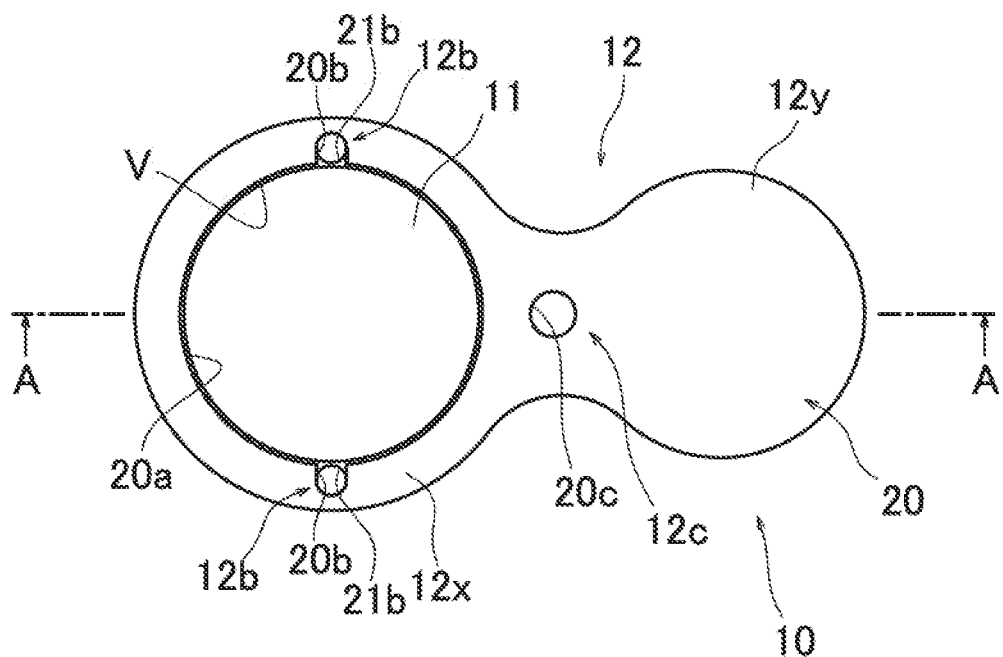
FIG. 3A and FIG. 3B are a plan view d a bottom view showing the electrode main body.
Figure 3B:
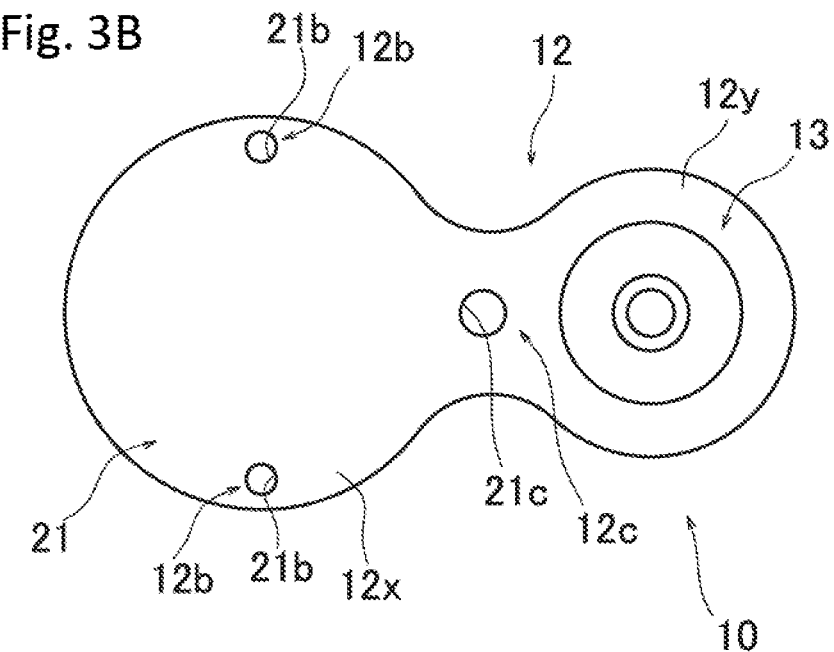

The electrode main body 10, specifically as shown in the exploded perspective view of FIG. 2, the plan view, and the bottom view of FIG. 3A and FIG. 3B, and the plan view, the right side view, the left wise view, and the sectional view of FIG. 4A-FIG. 4D, is composed of: a conductive gel 11 which is a conductive member formed in the shape of a thin disk; a retaining member 12 to retain the gel; and a spring hook 13 which is a connection terminal for connecting to the external device D.

The conductive gel 11 is made of a gel-like resin material having adhesiveness so as to be bonded with the retaining member 12 and the living body surface S, and in the embodiment, silver paste is employed in particular.

The retaining member 12 is a urethane sheet of which contour forms a 8-letter shape, in which a large circular part 12x and a small circular part 12y have been smoothly connected to each other, and a first retaining member 20 at the living body surface side and a second retaining member 21 at the opposite living body surface side of which shape is formed to be substantially identical thereto are formed by being bonded by a hot melt 22 of which shape is formed to be substantially identical thereto. At the time of this bonding, a flange-shaped head part 13a2 of a hook base 13a of the spring hook 13, which will be described later, is intended to be sandwiched between the first retaining member 20 and the second retaining member 21 of the small circular part 12y.

In the retaining member 12, a flat cylindrical retaining space V is formed to house the conductive gel 11 by: a cylindrical hole 20a of which diameter is substantially the same as that of the conductive gel 11, and which has been punched at the large circular part 12x of the first retaining member 20; and a surface 21a at the living body surface side of the second retaining member 21. In addition, the first retaining member 20 comprises cutouts 20b, 20b which are continuous to the hole 20a at two diagonal parts in the transverse direction, outward of the hole 20a; the second retaining member 21 comprises holes 21b, 21b that respectively penetrate in the living body surface direction in the corresponding positions to the cutouts 20b, 20b; and in the retaining member 12, through holes 12b, 12b which are open in the living body surface direction are formed of these cutouts 20b, 20b and holes 21b, 21b in the retaining member 12 (refer to FIG. 1). Further, in the retaining member 12, a through hole 12c which is open in the living body surface direction is formed of: a hole 20c which has been provided in a central part of the first retaining member 20; and a hole 21c which has been provided at a corresponding position of a central part of the second retaining member 21.

Incidentally, there is a need to precisely perform positioning when the first retaining member 20 and the second retaining member 21 are bonded with each other; and however, in the embodiment, as described above, three through holes are provided in one retaining member 12; and therefore, the cutouts 20b, 20b and hole 20c of the first retaining member 20 and the holes 21b, 21b, 21c of the second retaining member 21 are sequentially engaged into three guide pins (not shown) which have been installed at predetermined intervals, thereby making it possible to easily bond these retaining members.

In addition on the surface 21a at the living body surface side of the second retaining member 21, the conductive ink 21d is continuously printed all over the regions from the large circular part 12 side to the small circular part 12y side, and abuts against the surface on the conductive gel 11 and the opposite living body surface side of the head part 13a2 of the hook base 13a that constitutes the spring hook 13.

Figure 4A:
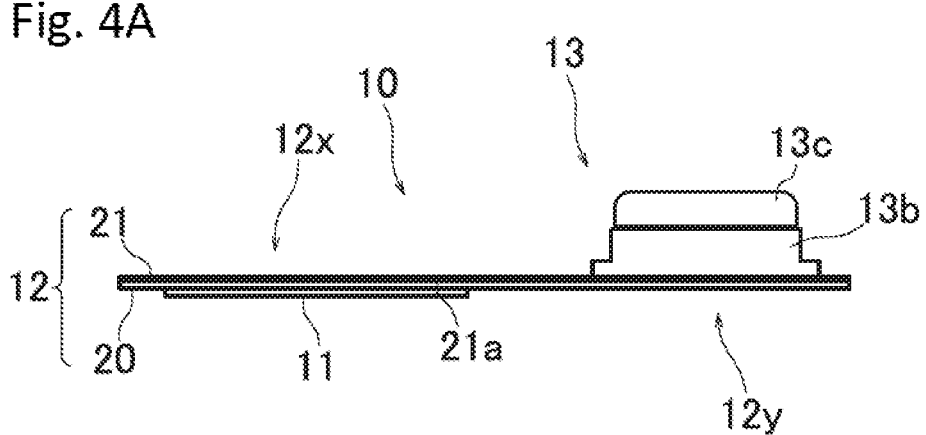
FIG. 4A-FIG. 4D are a front view, right side view, left side view, and a sectional view when cut at the position A-A of FIG. 2, showing the electrode main body.
Figure 4B:
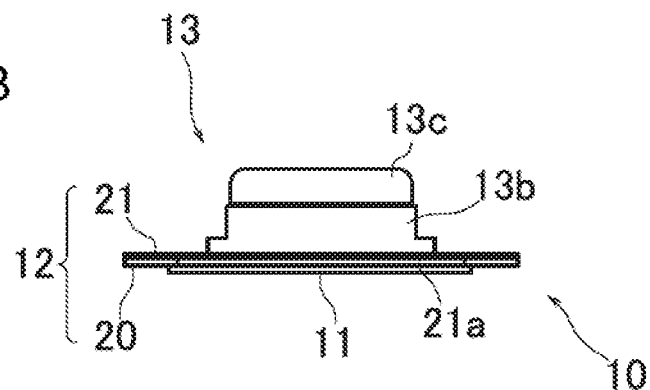
Figure 4C:
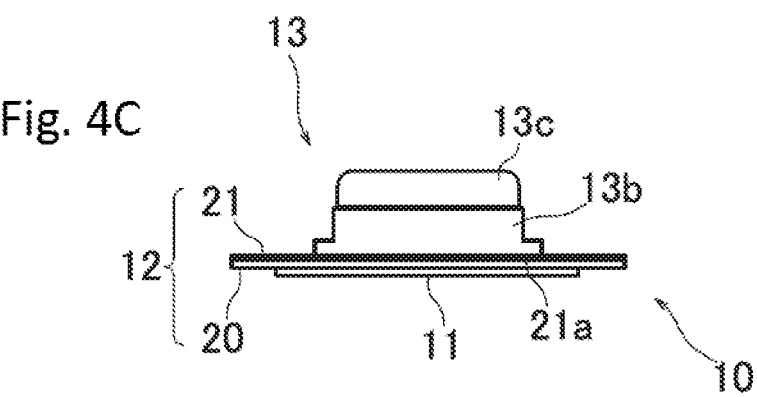
Figure 4D:
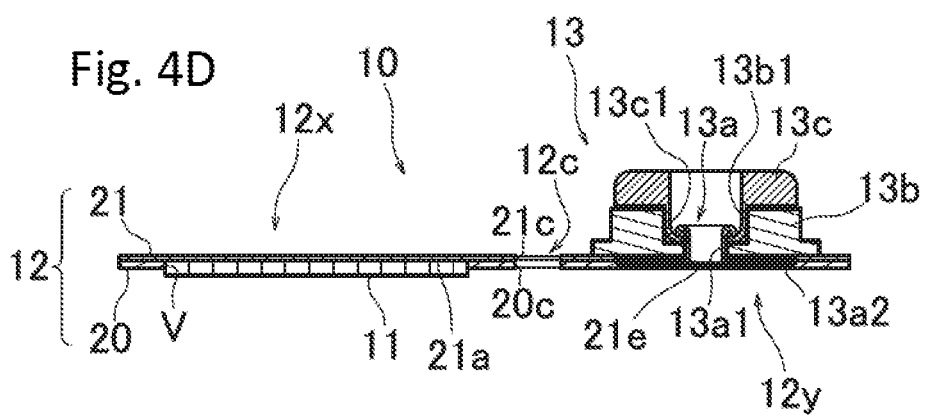

The spring hook 13 is composed of a hook base 13a having conductivity, a spacer 13b, and a spring part 13c having conductivity, and is mounted to the retaining member 12 by passing a protrusion part 13a1 of the hook base 13a through a hole 21e of the second retaining member 21 and a hole 13b1 of the spacer 13b and further inserting this protrusion part 13a1 into a recessed part 13c1 of the spring part 13c and then swaging it (refer to FIG. 4D). Thus, the hook base 13a and the spring part 13c having conductivity are electrically connected to each other, and the conductive ink 21d and the conductive gel 11 and the head part 13a2 of the hook base 13a described above are respectively electrically connected, so that the conductive gel 11 and the spring part 13c of the spring hook 13 are electrically connected to each other.

Incidentally, the surface at the living body surface side of the head part 13a2 of the hook base 13a is covered with the first retaining member 20 so as not to directly abut against the living body, and even in a case where the hook base 13a contains an allergen substance such as nickel, it does not affect the living body. In addition, the conductive ink 21d, living body surface side of which is covered with the first retaining member 20 and the conductive gel 11, is intended so as not to directly abut against the living body. In respect of the construction of the spring hook 13, a variety of structures are known and thus a detailed description thereof is omitted.

Figure 5A:
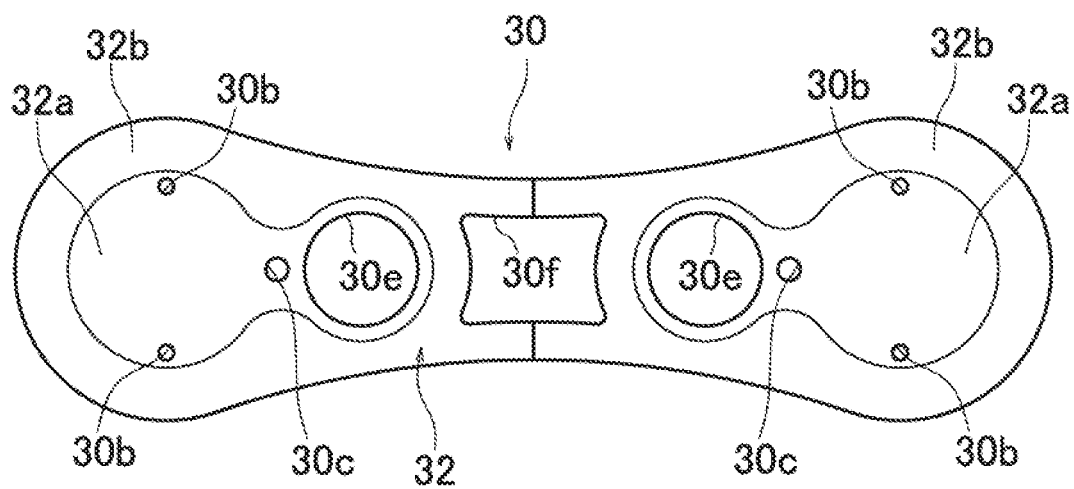
FIG. 5A-FIG. 5C are a plan view, a bottom view, and a schematic view showing a part when seen from a front view, showing an adhesive member of the biomedical electrode according to the first embodiment of the present invention.
Figure 5B:
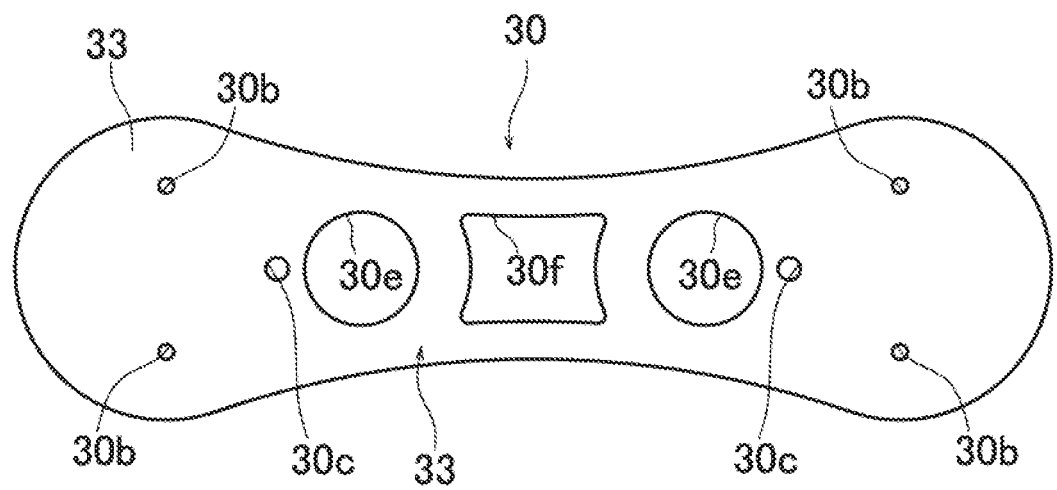
Figure 5C:
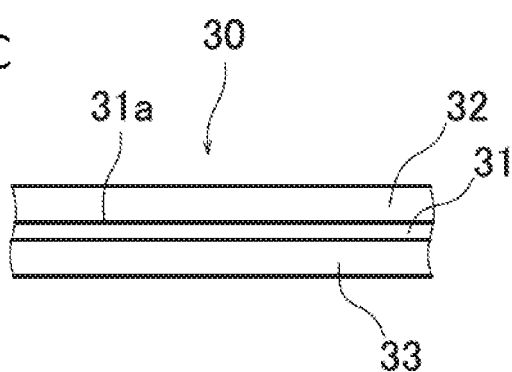

Next, the adhering member 30, as shown in the plan views, the bottom views, and the front view of FIG. 1 and FIG. 5A-FIG. 5C, is a sheet-shaped material forming a rectangular 8-letter shape, extending in the longitudinal direction so as to cover substantially all regions of the two electrode main bodies 10, 10 that have been spaced from each other at predetermined intervals, and has: a main body part 31, living body surface side of which is an adhesive surface 31a; and a sheet-shaped release paper 32 which is a protection member for protecting the adhesive surface 31a. In addition, the main body part 31 is formed in a shape of a thin film of which thickness is about 20 microns, and in order to support the main body part 31, as shown in FIG. 5C, the protection paper that is formed in the same shape is adhered at the opposite surface side as well. Incidentally, the front view of FIG. 5C is an enlarged view of a part of the adhesive member 30 and depicts the main body part 31 so as to be thicker than the real one. This adhesive member 30, as shown in FIG. 1, is adapted to be adhered in a manner in which the large circular part 12x of the retaining member 12 is more outward in the longitudinal direction than the small circular part 12y at a position at which the electrode main bodies 10, 10 are linearly symmetrical at both sides in the longitudinal direction with respect to a central part, in other words, in a manner in which the conductive gels 11, 11 have been arranged to be more outward in the longitudinal direction than the corresponding spring hooks 13, 13. In addition, in the adhesive member 30, the liquid through holes 30b to 30b, 30c, 30c are provided at the respective positions that correspond to the positions of the through holes 12b to 12b, 12c, 12c of the electrode main bodies 10, 10, and at the positions that correspond to the spring hook 13, the through holes 30e, 30e for protruding this spring hook 13 towards the opposite living body surface side are provided as shown in FIG. 1 and FIG. 5A-FIG. 5C. Further, at the central part of the adhesive member 30, that is more inward in the longitudinal direction than the two through holes 30e, 30e, a substantially rectangular through hole 30f which occupies about 50% or more in the width in the transverse direction is provided as well, and these liquid through holes 30b to 30b, 30c, 30c and the through holes 30e, 30e, 30f, 30f all penetrate all regions of the main body part 31, the release paper 32, and the protection paper 33.

The release paper 32 is divided into the shape along the retaining member 12 of the electrode main body 10, making it possible to separately release: first release papers 32a, 32a of which shape is substantially the same as that of the retaining member 12; and second release papers 32b which is the other portion. In addition, the second release paper 32b is also divided into two sections at the central part in the longitudinal direction.

Incidentally, the material for, and the contour shape of, the adhesive member 30, are not limited to those of the embodiment as long as the adhesive member has the functions as described above, a general tape for use in medical application or sports can be employed. It is to be kept in mind that the larger the area of the adhesive surface 31a of the adhesive member 30 is, the more difficult releasing is; and however, if the area is too large, it is difficult to release from the living body surface. Therefore, it is preferable that the adhesive member 30, while it is formed to be larger than the retaining member 12, be formed in the shape along the shape of the retaining member 12 so that the surface area is not so large.

In order to adhere the biomedical electrode 1 that is structured as described above to the living body surface S and then attach the external device D such as the heart rate monitor thereto, first, as shown in FIG. 1, the first release papers 32a, 32a of the adhesive member 30 are released and then the adhesive surface 31a of this portion is exposed, and the retaining member 12 is adhered to the exposed adhesive surface 31a while the spring hook 13 of the electrode main body 10 is protruded from the through hole 30e to the opposite living body surface side. At this juncture, it is easy to perform positioning as long as the liquid through holes 30b 30c at the adhesive member 30 side and the through holes 12cb, 12c at the retaining member 12 side are coincident with each other. Next, the second release paper 32b of the adhesive member 30 is released, and the biomedical electrode 1 is adhered so that the two conductive gels 11, 11 respectively abut against predetermined positions of the living body surface S. Lastly, the recessed spring parts 13c, 13c of the spring hooks 13, 13 of the electrode main bodies 10, 10 are respectively engaged with protrusive connection terminals Da, Da which are also referred to as "sheers" of the external device D, thereby making it possible to directly attach the external device D to the living body surface S. If the spring parts 13c, 13c, of the spring hooks 13, 13, are thus respectively engaged with the connection terminals Da, Da of the external device D, these constituent elements are electrically connected to each other, and the conductive gels 11, 11, of the biomedical electrode 1, and the external device D, are thereby electrically connected to each other.

Incidentally, in the biomedical electrode 1 that is adhered to the living body surface S in the sequential order as described above, the retaining members 12, 12 and the adhesive member 30 are independent of each other; and therefore, when the adhesive member 30 is released from the living body, the adhesive member is also released from the retaining members 12, 12, thereby making it possible to reuse the retaining member 12.

Figure 6:
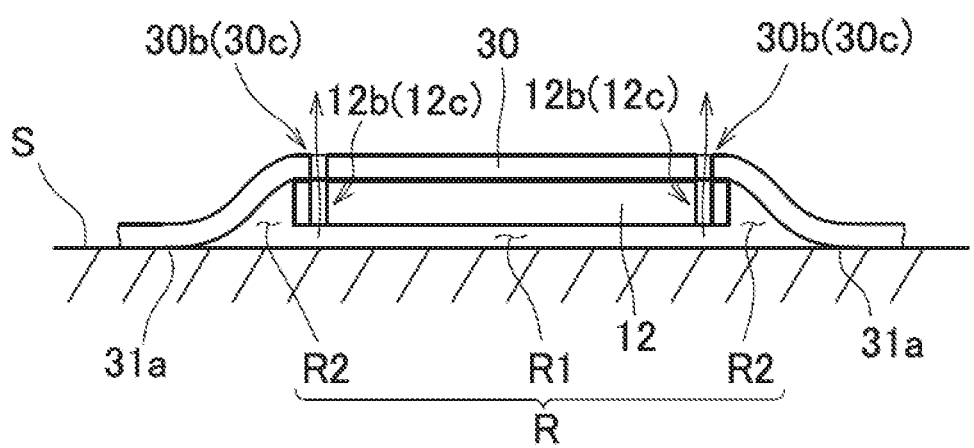
FIG. 6 is a schematic view when the biomedical electrode according to the first embodiment of the present invention is mounted to a living body surface.
Figure 7:
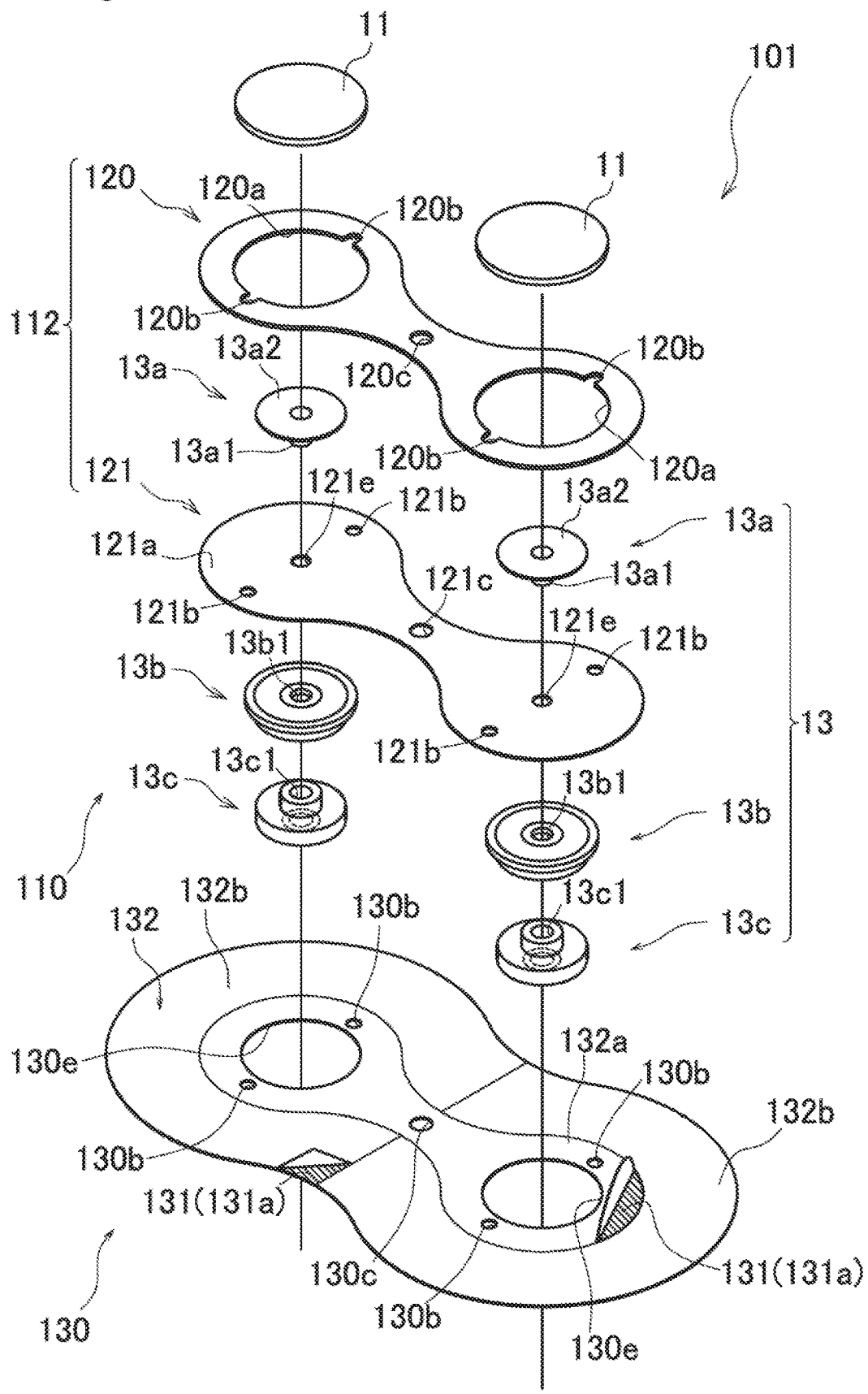
FIG. 7 is an exploded perspective view of a biomedical electrode according to a second embodiment of the present invention.
Figure 8A:
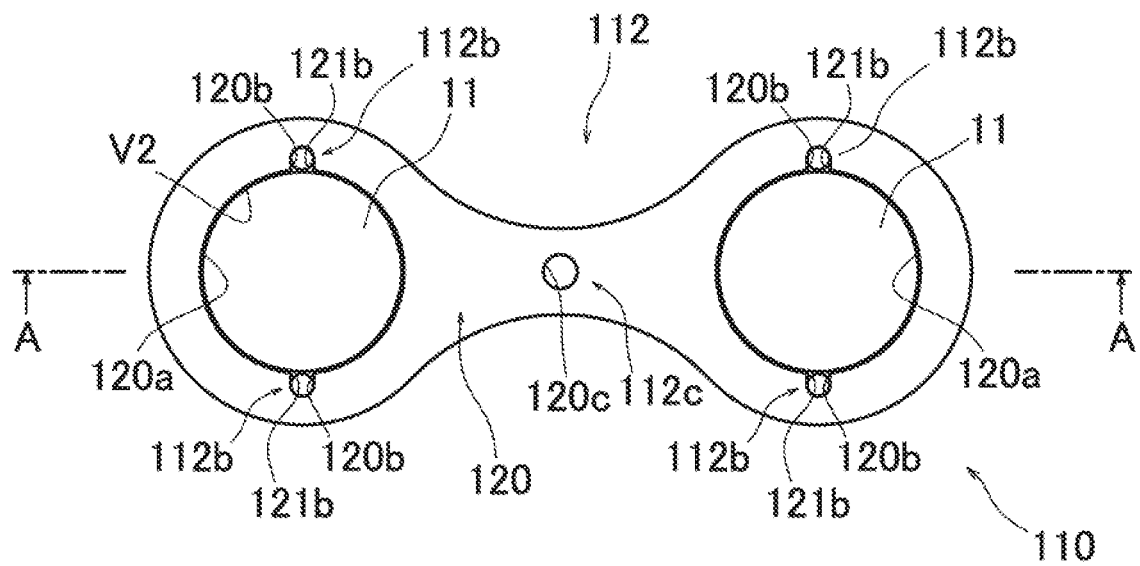
FIG. 8A and FIG. 8B are a plan view and a bottom view showing an electrode main body of the biomedical electrode.
Figure 8B:
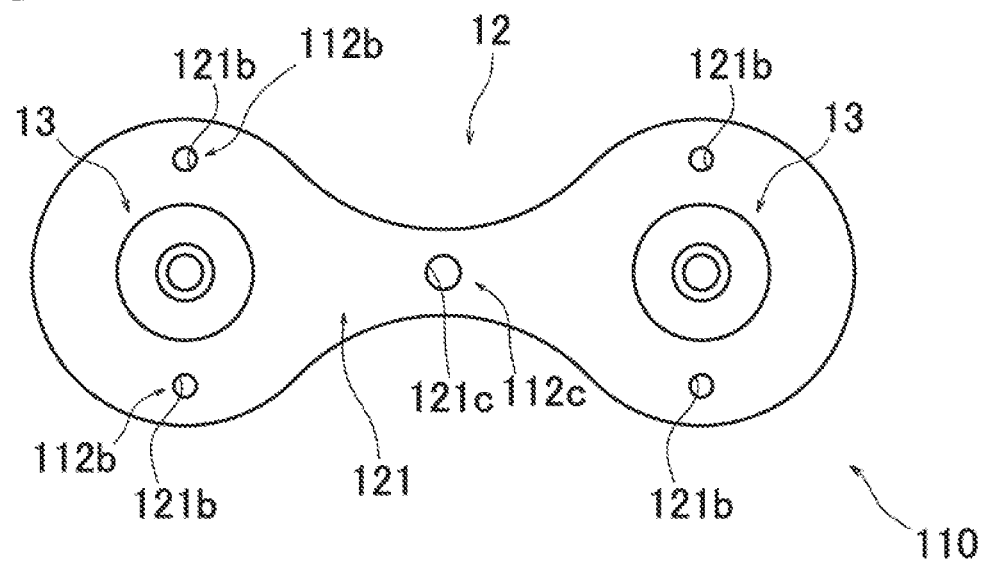
Figure 9A:
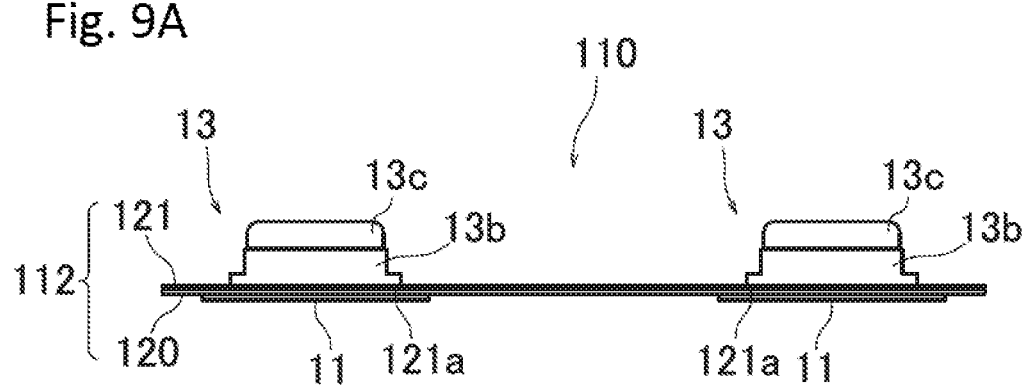
FIG. 9A-FIG. 9C are a front view, a side view, and a sectional view when cut at the position A-A of FIG. 8, showing the electrode main body.
Figure 9B:
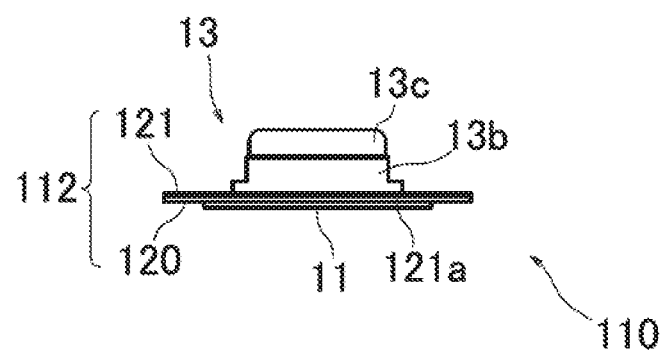
Figure 9C:
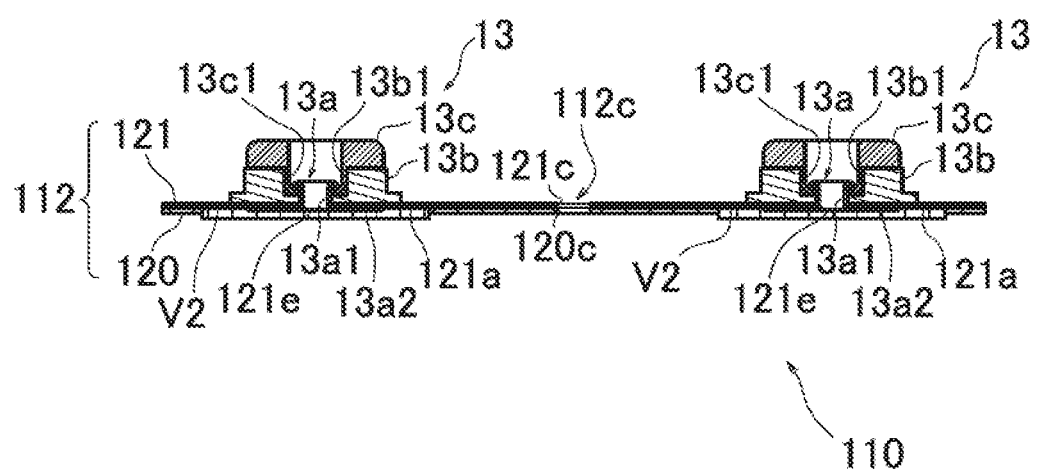
Figure 10A:
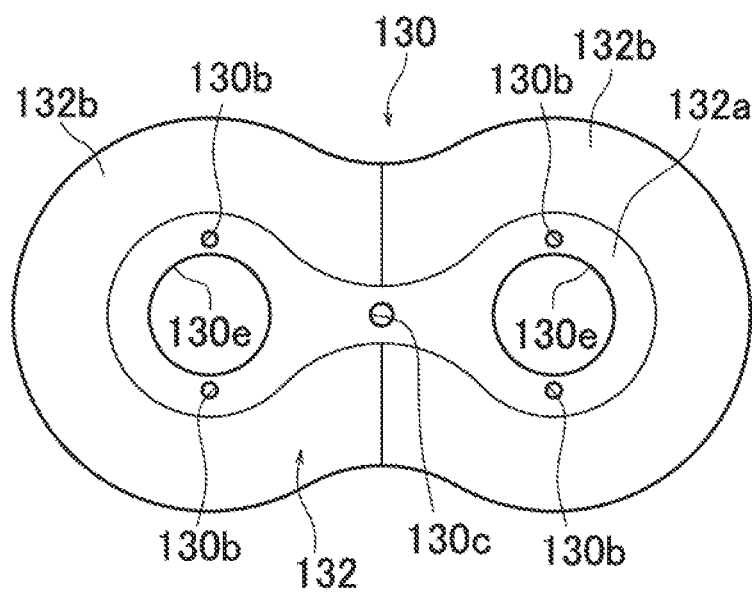
FIG. 10A-FIG. 10C are a plan view, a bottom view, and a schematic view showing a part when seen from a front side, showing an adhesive member of the biomedical electrode according to the second embodiment of the present invention.
Figure 10B:
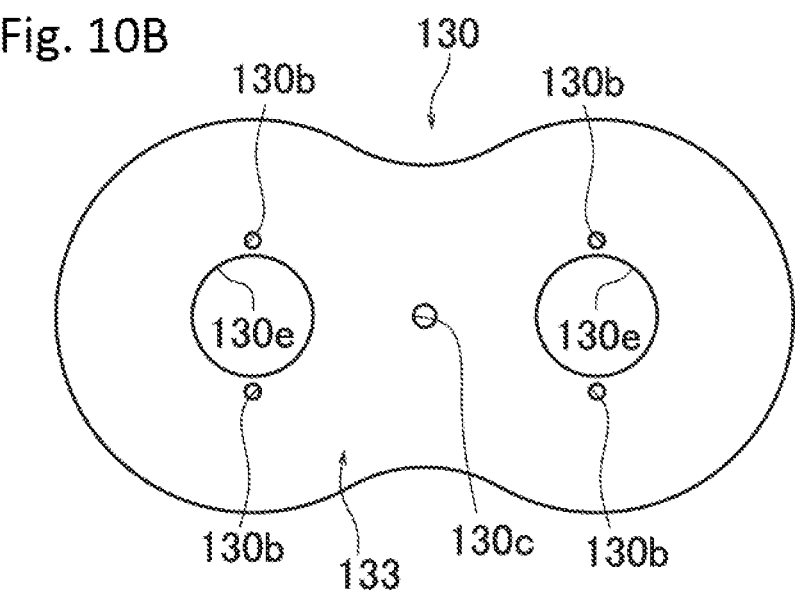
Figure 10C:
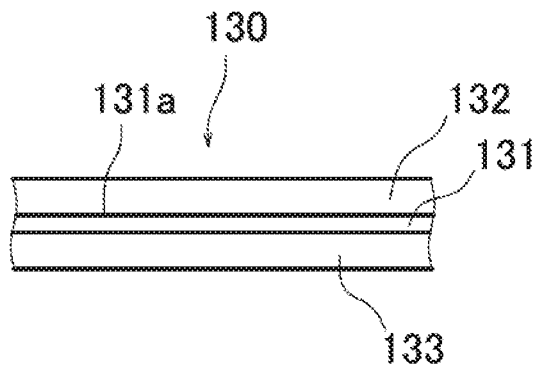

If the biomedical electrode 1 is adhered to the living body surface S, the adhesive force of the adhesive member 30 does not take effect between the retaining member 12 and the living body surface S; and therefore, as shown in the schematic view of FIG. 6, between the living body surface S and the retaining member 12, an internal space R is formed to be composed of: a space R1 which is formed immediately underneath the retaining member 12; and a very small space R2 which is continuous to this space R1 and which is wedge-shaped in a cross section formed at the periphery of the retaining member 12 by the thickness of the retaining member 12. Incidentally, although the conductive gel 11 is present in the space R1, such gel is not shown in FIG. 6. In addition, in a state in which the biomedical electrode 1 is adhered, if a long period of time elapses or if exercise is performed, sweat is accumulated in this internal space R. If the sweat is thus accumulated in the internal space R, the adhesive force of the adhesive surface 31a of the adhesive member 30 that is adjacent to the internal space R lowers due to the moisture of the accumulated sweat, and there may also be a case in which the conductive gel 11 inflates; and therefore, the amount of the sweat increases, whereby there is an apprehension that the adhesive member 30 is released from the inside from the living body surface S. However, the liquid through holes 30b, 30b, 30c are provided in the biomedical electrode 1 of the embodiment, and these liquid through holes 30b, 30b, 30c respectively communicate with the internal space R via the through holes 12b, 12b, 12c of the retaining member 12; and therefore, the sweat that is accumulated in the internal space R is discharged to the opposite living body surface side more significantly than the adhesive member 30 through these through holes 12b, 12b, 12c and liquid through holes 30b, 30b, 30c. Hence, in the biomedical electrode 1 of the embodiment, the accumulation of the sweat in the internal space R is restrained, making it possible to restrain the release of the adhesive member 30. Incidentally, there is a possibility that sweat is accumulated in a retaining space V in which the conductive gel 11 is to be retained; and however, in the embodiment, the cutouts 20b, 20b of the first retaining member 20, that form the through holes 12b, 12b of the retaining member 12, communicate with the retaining space V; and therefore, the accumulation of the sweat in the retaining space V is restrained as well.

In addition, the through hole 30f is provided at the central part of the adhesive member 30; and therefore, the sweat that is produced on the living body surface S and at the central part of the adhesive member 30 is not allowed to be accumulated inside of the adhesive member 30 while a securing force of the electrode main bodies 10, 10 and the external device D is maintained, and the width of a portion of liking the two electrode main bodies 10, 10 is reduced, thereby making it possible to operate the two electrode main bodies 10, 10 somewhat independently; and hence, it is possible to improve traceability of the electrode main bodies 10, 10 with respect to the living body surface S as well. In addition, by providing the through hole 30f, the area of adhering the adhesive member 30 to the living body surface S is reduced, thus making it possible to restrain an increase in tension feeing of the living body surface S, which leads to an increase in wearing comfort, and further, it is also possible to reduce a burden on the living body surface S when the adhesive member 30 is released from the living body surface S after use.

As described above, the biomedical electrode of the embodiment has: the conductive gels 11, 11 that are conductive members; the retaining members 12, 12 to retain the conductive gels 11, 11; and the adhesive surface 31a, and comprises the sheet-shaped adhesive member 30 to adhere the conductive gels 11, 11 to the living body surface S via the retaining members 12, 12, and the adhesive member 30 is formed in an enough size to cover substantially all regions of the retaining members, 12, 12, and is configured to have the liquid through holes 30b to 30b, 30c, 30c to discharge the sweat that is accumulated in the internal spaces R, R formed between the living body surface S and the retaining members 12, 12.

According to such a configuration, even if the living body takes a hard action, it is possible to restrain the displacement or release of the conductive gels 11, 11. In addition, the electrode is merely secured by the adhesive member 30; and therefore, such discomfort as felt in the case where the electrode is mounted by the belt does not arise, and in the case where the electrode is mounted at the time of sports as well, it is possible to concentrate on the athletic sports. Further, the electrode has the liquid through holes 30b, 30b, 30c, 30c which discharge the seat accumulated in the internal spaces R, R between the living body surface S and the retaining members 12, 12, and the sweat that is accumulated in the internal spaces R, R is pushed out from the liquid through holes 30b to 30b, 30c, 30c due to the action of the living body, thus making it possible to restrain the release of the adhesive member 30 from the portion that is adjacent to the internal spaces R, R due to the sweat accumulated in the internal spaces R, R. In addition, it is also possible to prevent electric conduction of the two conductive gels 11, 11 due to the moisture of the sweat.

In addition, the retaining members 12, 12 retains the conductive gels 11, 11 at the living body surface side, and at the opposite surface side, the spring holes 13, 13 that are the connection terminals to electrically connect to the conductive gels 11, 11 are provided; the adhesive member 30 has the through holes 30e, 30e to protrude the spring hooks 13, 13, and is releasable from the retaining members 12, 12; and therefore, it is possible to mount or demount the external device D in a state in which the conductive gels 11, 11 are mounted to the living body surface S, and when the biomedical electrode 1 is repeatedly mounted to, or demounted from, the living body surface S, only the adhesive member 30 is replaced with its replacement to thereby enable reuse of the retaining members 12, 12.

Further, in the adhesive member 30, the adhesive surface 31a is exposed by releasing the release paper 32 that is the sheet-shaped protection members to protect the adhesive surface 31a, and the release paper 32 is divided into the first release papers 32b, 32b along the retaining members 12, 12 and the second release papers 32b, 32b that are the other portions, thus making it possible to easily perform positioning at the time of attachment to the adhesive member.

In addition, the through holes 12b to 12b, 12c, 12c are provided in the retaining members 12, 12, and the liquid through holes 30b to 30b, 30c, 30c that are provided in the adhesive member 30 respectively overlap the through holes 12b to 12b, 12c, 12c that have been provided in the retaining members, 12, 12 to thereby communicate with the internal spaces R, R; and therefore, it is easier to perform positioning when the retaining members 12, 12 are adhered to the adhesive member 30 while restraining the release of the adhesive member 30 due to the sweat.

In addition, the retaining members 12, 12 forms a dual structure in which the first retaining members 20, 20 at the living body surface side and the second retaining members 21, 21 at the opposite living body surface side are bonded with each other; the cylindrical retaining spaces V, V are formed of the holes 20a, 20a that have been provided in the first retaining members 20, 20 and the surfaces 21a, 21a at the living body surface side of the second retaining members 21, 21; and the conductive gels 11, 11 is retained in the retaining spaces V, V; and therefore, the conductive gel is stably retained and the internal spaces R, R between the retaining members 12, 12 and the living body surface S are increased by the thickness of the conductive gel, making it possible to restrain easy accumulation of the sweat in the internal spaces R, R.

Further, the retaining members 12, 12 each comprises three through holes 12b, 12b, 12c; and therefore, accumulation of the sweat in the internal spaces R, R is more effectively restrained, making it possible to easily perform positioning when the first retaining members 20, 20 and the second retaining members 21, 21 are bonded with each other.

In addition, the two conductive gels 11, 11 are provided; the two conductive gels are arranged to be more outward than the corresponding connection terminals 13, 13; and the conductive gels 11, 11 and the corresponding connection terminals 13, 13 are electrically connected to each other by the conductive inks 21d, 21d that have been printed on the retaining members 12, 12; and therefore, in a case where the external device D such as the heart rate monitor is directly attached to the living body surface S, it is possible to improve traceability of the conductive gels 11, 11 with respect to the living body surface S, and restrain the release of the conductive gels 11, 11 from the living body surface S.

Moreover, the retaining member 12 is also separated as to each conductive gel 11, thus making it possible to improve traceability of the conductive gels 11, 11 with respect to the living body surface S.

Second Embodiment

Next, a biomedical electrode 101 according to a second embodiment of the present invention will be described with reference to FIG. 7 to FIG. 10A-FIG. 10C. As shown in the exploded perspective view of FIG. 7, this embodiment is mainly different from the first embodiment in that one electrode main body 110 (refer to the plan view and the bottom view of FIG. 8A and FIG. 8B, the front view, the side view and the sectional view of FIG. 9A-FIG. 9C) is composed of two conductive gels 11, 11 and one retaining member 112 to retain these gels, and this electrode main body 110 is adhered to one adhesive member 130 (refer to the plan view, the bottom view, and front view of FIG. 10A-FIG. 10C) to thereby constitute one biomedical electrode 101. Incidentally, in the embodiment, the constituent elements that are common to those of the first embodiment are basically designated by same reference numerals, and a description of these constituent elements is omitted.

The retaining member 112 of the biomedical electrode 101, as shown in FIG. 7 to FIG. 9A-FIG. 9C, is a nonconductive sheet which is linearly symmetrical in the longitudinal direction, contour of which forms an 8-letter shape, and is formed by being bonded by a hot melt, which is not shown, in a state in which a first retaining member 120 at a living body surface side and a second retaining member 121 at an opposite living body surface side of which shape is formed to be substantially identical thereto have sandwiched a flange-shaped head part 13a2 of hook bases 13a, 13a of spring hooks 13, 13 therebetween. Incidentally, in the biomedical electrode 101, conductive gels 11, 11 and the head part 13a2 of the hook bases 13a, 13a of the spring hooks 13, 13 abut against each other, and these constituent elements are thereby electrically connected to each other (refer to FIG. 9C).

In the retaining ember 112, a flat, cylindrical retaining space V2 to house the conductive gels 11, 11 is formed of cylindrical holes 120a, 120a which have been punched at both sides in the longitudinal direction of the first retaining member 120, the head part 13a2 of the hook base 13a, and a surface 121a at the living body surface side of the second retaining member 121. In addition, the first retaining member 120 has cutouts 120b to 120b which are continuous to the holes 120a, 120a in the respective diagonal two parts in the transverse direction, outward of the holes 120a, 120a; the second retaining member 121 comprises the holes 121b to 121b which penetrate in the living body surface direction in the respective positions that correspond to these cutouts 120b to 120b; and in the retaining member 112, a through hole 112b which is open in the living body surface direction is formed of these cutouts 120b to 120b and the holes 121b to 121b. Further, in the retaining member 112, a through hole 112c which is open in the living body surface direction is formed of: a hole 120c which has been provided at a central part of the first retaining member 120; and a hole 121c which has been provided at a corresponding position of a central part of the second retaining member 121c. In addition, holes 121e, 121e to insert the hook bases 13a, 13a are formed at the respective positions which correspond to centers of the holes 120a, 120a of the first retaining member 120.

On the other hand, an adhesive member 130, as shown in FIG. 7 and FIG. 10A-FIG. 10C, comprises: a main body part 131 which forms an 8-letter shape extending in the longitudinal direction so as to cover the electrode main body 110 and which has the adhesive surface 131a at the living body surface side; and a sheet-shaped release paper 132 of which shape is formed to be the same as that of this main body part 131, for protecting an adhesive surface 131a. In this adhesive member 130, liquid through holes 130b to 130b, 130c are provided in the respective positions which correspond to the positions of the through holes of the electrode main body 110, and through holes 130e, 130e for protruding this spring hook 13 towards the opposite living body surface side are provided in the respective positions that correspond to the positions of the through holes of the electrode main body 110. In addition, the release paper 132 is divided into the shape along the retaining member 112 of the electrode main body 110, making it possible to separately release a first release paper 123a of which shape is formed to be substantially the same as that of the retaining member 112 and a second release paper 132b which is the other portion from each other.

By employing the configuration as described above, it is possible to attain the advantageous effect which is equivalent to that of the first embodiment by the biomedical electrode 101 of the second embodiment as well. Further, one retaining member 112 retains the two conductive gels 11, 11, thus making it possible to reduce the cumbersomeness in mounting the retaining member 112 to the adhesive member 130.

Incidentally, specific structures of the respective constituent elements are not limited to the embodiments described above.

Figure 12:
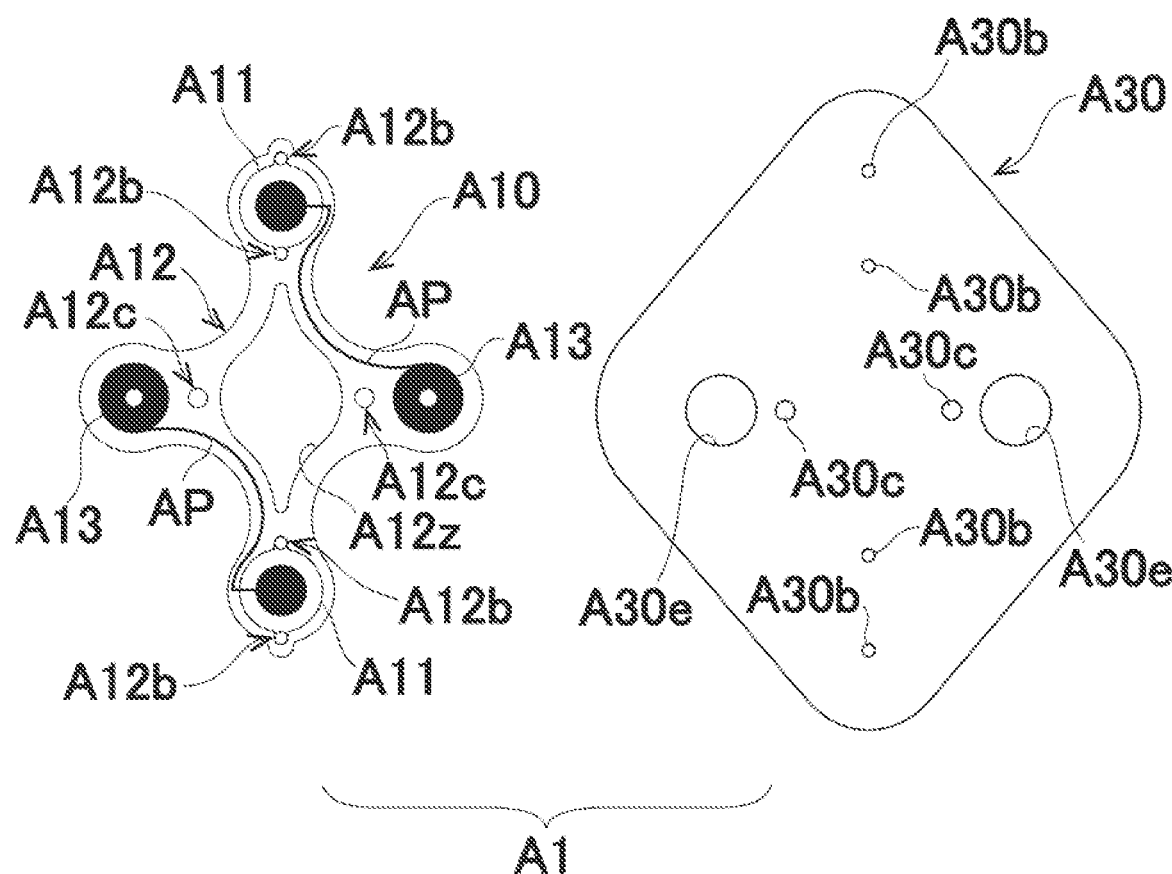
FIG. 12 is a structural view of a biomedical electrode showing a modification example of the present invention.

For example, in the first embodiment, the biomedical electrode 1 was mainly composed of the two electrode main bodies 10, 10 and one adhesive member 30 and was mounted by being adhered to the living body surface S while the electrode main bodies 10, 10 are adhered to the adhesive member 30, and each electrode main body 10 was composed of: the conductive gel 11; the retaining member 12 to retain this gel; and the spring hook (connection terminal) 13 that is a connection terminal for connecting to the external device D; and however, as shown in FIG. 12, a biomedical electrode A1 may be composed of one electrode main body A10 and one adhesive member A30 as a whole. In this case, the electrode main body 10 is characterized in that: a pair of conductive gels A11 are disposed to oppose to each other at predetermined intervals; a pair of spring hooks (connection terminals) A13 are disposed to oppose to each other at predetermined intervals in a direction crossing (orthogonal to) the opposite direction of the conductive gel A11; and these constituent elements are retained by a cross-shaped retaining member A12 having a punched hole A12z at a center thereof. That is, of the retaining member 12, the conductive gel A11 is disposed at the living body surface side; the spring hook A13 is disposed at the opposite living body surface side; and the conductive gel A11 and the spring hook A13 are connected to each other via a printed wiring Ap which has been provided at a part of the retaining member. The adhesive member A30 has through holes A30e, A30e which respectively protrude the spring hooks A13, A13, and is releasable from the retaining member A12.

The adhesive member A30 is formed in an enough size to cover substantially all regions of the retaining member 12, and has liquid through holes A30b to A30b, A12c, A12c which discharge the sweat accumulated in an internal space formed between the living body surface and the retaining member 12; and in the retaining member A12, through holes A12b to A12b, A30c, A12c are provided; and further, the liquid through holes A30b to A30b, A30c, A30 that have been provided in the adhesive member A30 respectively overlap the through holes A12b to A12b, A12c, A12c that have been provided in the retaining member A12 to thereby communicate with the internal space.

Figure 13A:
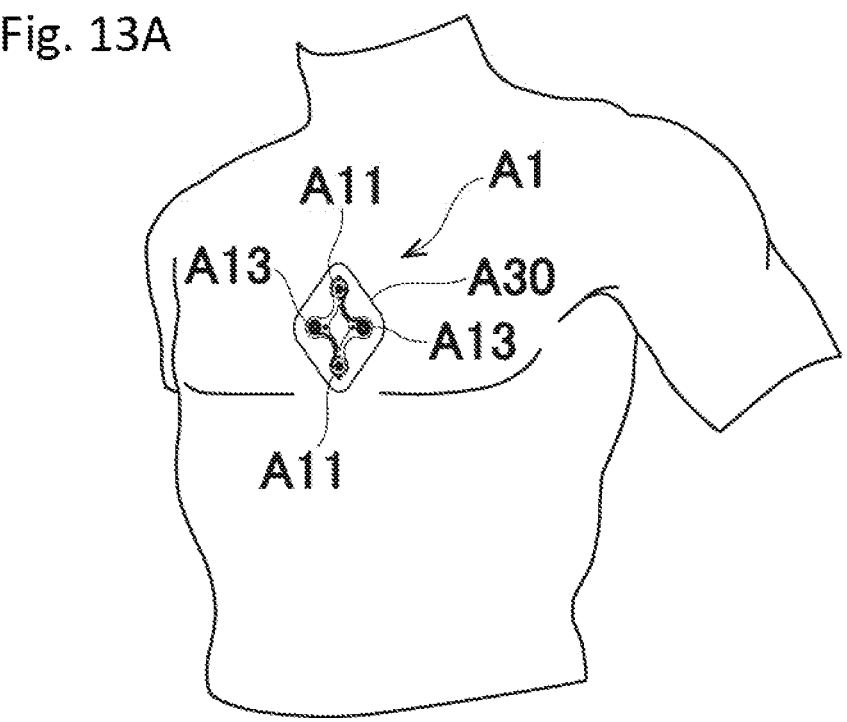
FIG. 13A and FIG. 13B are a view showing a use state of the biomedical electrode.
Figure 13B:
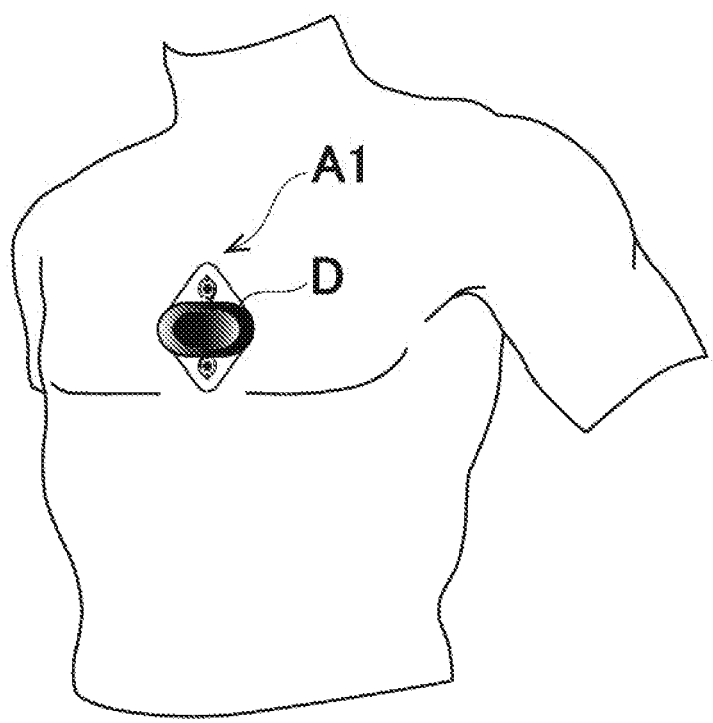

According to such a configuration, the functions and advantageous effects similar to those of the first embodiment are attained. Moreover, even if the left and right pectoral muscles take a non-uniform action, as shown in FIG. 13A, the spring hook A13 is positioned inside of the left and right pectoral muscles, the conductive gel A11 is vertically adhered to the living body surface along the centerline of the body, and the adhered gel is then covered with the adhesive member A30, thereby making it difficult for the vertically adhered conductive gel A11 to move while being affected by the movement of the left and right pectoral muscles; and therefore, as shown in FIG. 13B, an external device D such as a heart rate monitor is mounted to the left and right spring hooks A13, thereby making it possible to perform measurement of a heart rate with high precision or the like through the conductive gel A11. It is more advantageous that a punched hole 12z of which aperture is a comparatively large can be provided at a center as well. Moreover, the retaining member 12 integrally retains a pair of conductive gels A11 and a pair of spring hooks A13; and therefore, the convenience of handing thereof is more remarkably improved.

Figure 11:
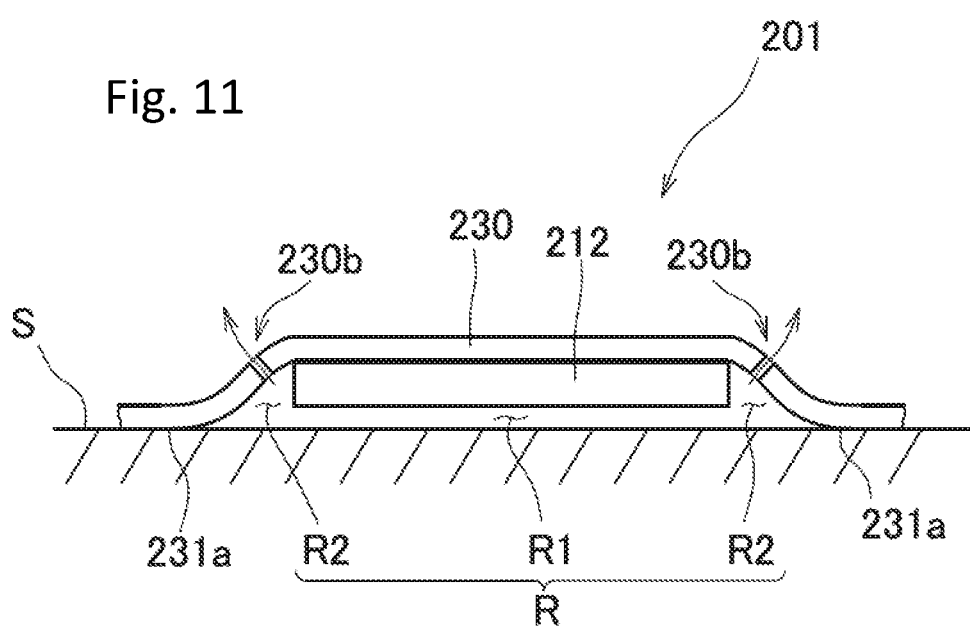
FIG. 11 is a schematic view when a biomedical electrode according to another embodiment of the present invention is mounted to a living body surface.

In addition, although the embodiments described above, the through holes 20b, 20c (120b, 120c) that had been provided in the retaining members 12 (120) and the liquid through holes 30b, 30c (130b, 130c) of the adhesive members 30 (130) were adapted to communicate with each other so as to thereby discharge the sweat that had been produced in the internal space R to the outside, like a biomedical electrode 201 shown in FIG. 11, a liquid through hole 230b is provided in the vicinity of a portion of adhering a retaining member 212 of an adhesive member 230 without providing a through hole in the retaining member 212, thereby making it possible to discharge the sweat that has been accumulated in the internal space R from the liquid through hole 230b via a small space R2 which is produced at the periphery of the retaining member 212 by the thickness of the retaining member 212 as well.

In addition, although in the embodiments described above, the retaining members 12 (112, 212) were formed to be larger than the conductive gel 11, it is possible to form a retaining member to be smaller than a conductive gel as well.

Further, although in the embodiment described above, three liquid through holes were provided as to one electrode main body 20, it is sufficient if the adhesive member comprises at least one liquid through hole in order to discharge the sweat that is accumulated in the internal space R. In this case also, a pressure is applied into the internal space R by the movement the living body, and the sweat in the internal space R is discharged to the outside through the liquid through hole. Incidentally, in a case where only one liquid through hole is provided, it is preferable that the liquid through hole be formed to be positioned in the vicinity of the lowest part of the internal space R when the biomedical electrode has been mounted to the living body surface. Of course, it is possible to provide four or more liquid through holes as well.

In addition, although the biomedical electrodes 1, 101 in the embodiments described above had two conductive gels 11 which are conductive members, it is possible to apply the present invention to a biomedical electrode which comprises only one conductive member as well.

In addition, although in the embodiments described above, the retaining members 12 (112) and the adhesive members 30 (130) were structured to be detachable from each other, there may be constructed a biomedical electrode in which a retaining member and an adhesive member have been integrated with each other by swaging a spring hook in a state in which the retaining member and the adhesive members have been pinched.

Further, although the embodiments described above presupposed a construction in which the external device D such as the heart rate monitor is directly attached to the biomedical electrode, it is possible to electrically connect a biomedical electrode to an external device via a cable as well.

In respect of another structure also, various modifications are possible without departing from the spirit of the present invention.

DESCRIPTION OF REFERENCE NUMERALS

R . . . Internal space
S . . . Living body surface
1, 101, 201, A1 . . . Biomedical electrodes
11, A11 . . . Conductive gels (conductive members)
12, 112, 212, A12 . . . Retaining members
12b, 12c, 112b, 112c, A12b, A12c . . . Through holes
13, 13A . . . Spring hooks (connection terminals)
20, 120 . . . Holes
20a, 120a . . . First retaining members
21a, 121 . . . Second retaining members
21a, 121a . . . Surfaces
21d . . . Conductive ink
30, 130, 230, A30 . . . Adhesive members
30b, 30c, 130b, 130c, 230b, 230c, A30b, A30c . . . Liquid through holes
30e, 130e, A30e . . . Through holes
31a, 131a . . . Adhesive surfaces
32, 132 . . . Release papers (protection members)

The invention claimed is:

1. A biomedical electrode to be attached to a target, the biomedical electrode comprising:
a conductive member;
a retaining member larger than the conductive member, the retaining member having a retaining space in which the conductive member is retained; and
an adhesive member having one surface, an entirety of which is an adhesive surface, the one surface adhering to the retaining member to cover at least an edge of the retaining member such that a periphery of the one surface, that is beyond the retaining member and surrounds the retaining member, is to be adhered to the target,
wherein the conductive member, the retaining member and the adhesive member in order forms a mutually overlapping region from a side closer to a target to be attached,
wherein an internal space is formed between an area of the conductive member adapted to contact the target and the retaining member,
wherein the adhesive member has a first through hole to discharge a liquid which is accumulated in the internal space.

2. The biomedical electrode according to claim 1, further comprising a connection terminal wherein the retaining member also retains the connection terminal so as to electrically connect to the conductive member,
the adhesive member has a second through hole, and
the connection terminal is protruded through the second through hole, and
the adhesive member is releasable from the retaining member.

3. The biomedical electrode according to claim 1, wherein the adhesive member comprises a sheet-shaped protection member for protecting the adhesive surface, the sheet-shaped protection member releasable from the adhesive member, and
the protection member is divided into a shape along the retaining member.

4. The biomedical electrode according to claim 1, wherein a second through hole is provided in the retaining member, and
the first through hole that is provided in the adhesive member overlaps the second through hole that is provided in the retaining member to thereby communicate with the internal space.

5. The biomedical electrode according to claim 1, wherein the retaining member comprises a dual structure in which a first retaining member and a second retaining member are bonded with each other, a retaining space is formed by a hole provided in the first retaining member and a surface of the second retaining member such that the conductive member is retained in the retaining space.

6. The biomedical electrode according to claim 5, wherein the retaining member comprises at least three second through holes.

7. The biomedical electrode according to claim 1, further comprising two main bodies, each of the main bodies comprising the conductive member, the retaining member and a connection terminal, wherein in each of the main bodies, the conductive member is arranged to be more outward than the connection terminal, and wherein in each of the main bodies, the conductive member is electrically connected to the connection terminal by conductive ink which has been printed on the retaining member.

\* \* \* \* \*